United States Patent [19]
Bock et al.

[11] Patent Number: 5,324,726
[45] Date of Patent: Jun. 28, 1994

[54] BENZODIAZEPINE ANALOGS

[75] Inventors: Mark G. Bock, Hatfield; Ben E. Evans; Roger M. Freidinger, both of Lansdale, all of Pa.

[73] Assignee: Merck & Co., Inc., Rahway, N.J.

[21] Appl. No.: 968,624

[22] Filed: Oct. 29, 1992

Related U.S. Application Data

[63] Continuation-in-part of Ser. No. 824,764, Jan. 17, 1992, abandoned, which is a continuation of Ser. No. 621,500, Dec. 7, 1990, abandoned, which is a continuation-in-part of Ser. No. 452,012, Dec. 18, 1989, abandoned.

[51] Int. Cl.$^5$ .............. A61K 31/55; C07D 243/24; C07D 243/22; C07D 243/16
[52] U.S. Cl. .................. 514/221; 540/504; 540/505; 540/509; 540/510; 540/512; 540/513; 540/514; 540/572; 540/573
[58] Field of Search .............. 514/221; 540/504, 505, 540/509, 510, 512, 513, 514, 572, 573

[56] References Cited

U.S. PATENT DOCUMENTS
4,820,834  4/1991  Evans et al. ................. 540/504

FOREIGN PATENT DOCUMENTS
0304223  2/1989  European Pat. Off. .
411668  2/1991  European Pat. Off. .

OTHER PUBLICATIONS
Bradwejn, et al., *Enhanced Sensitivity to Cholecystokinin Tetrapeptide in Panic Disorder*, Soc. Neurosci. Abstr. 14(1), p. 291, (1988).

(List continued on next page.)

*Primary Examiner*—Mark L. Berch
*Attorney, Agent, or Firm*—Mark R. Daniel; Joseph F. DiPrima

[57] ABSTRACT

Benzodiazepine analogs of the formula:

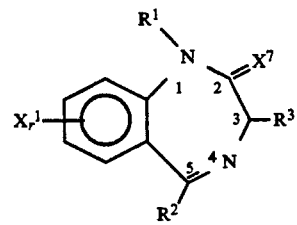

wherein:
$R^3$ is

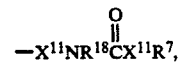

$-NH(CH_2)_{2-3}NHCOR^7$,

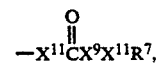

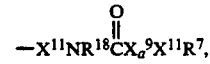

or $-X^{11}NR^{18}SO_2(CH_2)_qR^7$;
$R^7$ is O,S,HH, or $NR^{15}$ with the proviso that $X^7$ can be $NR^{15}$ only when $R^1$ is not H.

are disclosed which are antagonists of gastrin and cholecystokinin (CCK) with enhanced aqueous solubility and have properties useful in the treatment of disorders of gastric secretion, appetite regulation, gastrointestinal motility, pancreatic secretion, and dopaminergic function, as well as in treatment producing potentiation of morphine and other opiate analgesics.

4 Claims, No Drawings

OTHER PUBLICATIONS de Montigny, *Cholecystokinin Tetrapeptide Induces Panic Attacks in Healthy Volunteers*, Soc, Neurosci. Abstr. 14(1), p. 291, (1988).

Bradwejn, et al., *Benzodiazepines Antagonize Cholecystokinin–Induced Activation of Rat Hippocampal*, Neurones, Nature 312, p. 22, (1984).

de Montigny, *Cholecystokinin Tetrapeptide Induces Panic-like Attacks in Healthy Volunteers*, Arch. Gen. Psychiatry, 46, pp. 511-517, (1989).

Dourish, et al., *Enhancement of Morphine Analgesia and Prevention of Morphine Tolerance in the Rat by the Cholecystokinin Antagonist L-364*, 718 Pharm. 147, pp. 469-472, (1988).

Bouthillier, et al., *Long-term Benzodiazepine Treatment Reduces Neuronal Responsiveness to Cholecystokinin: an Electrophysiological Study in the Rat*, Eur. Jour. Pharm. 151, No. 1, pp. 135-138, (1988).

O'Neill et al. *Morphine Induced Analgesia in the Rat Paw Pressure Test is Blocked by CCk and Enhanced by the CCK Antogonist* MK-329, Neuropharmacology 28, No. 3, pp. 243-247 (1989).

Chang, et al., *Biochemical and Pharmacological Characterization of an Extremely Potent and Selective Nonpeptide Cholecystokinin Antagonist*, Proc. Natl. Sci., 83, pp. 4923-4926 (1986).

BENZODIAZEPINE ANALOGS

CROSS-REFERENCE

This is a continuation-in-part application of U.S. Ser. No. 07/824,764 filed Jan. 17, 1992, now abandoned which is a continuation of U.S. Ser. No. 07/621,500 filed Dec. 7, 1990, now abandoned which is a continuation-in-part application of U.S. Ser. No. 07/452,012 now abandoned filed Dec. 18, 1990 now abandoned.

Starting materials for the compounds of Formula I are prepared and described in U.S. Pat. No. 4,820,834 and B. Evans et al., J. Med. Chem. 31, 2235–2246 (1988), both incorporated by reference for these purposes. This application is related to Merck cases 18023 (U.S. Ser. No. 852,478, filed Mar. 18, 1992) and 18028 (U.S. Ser. No. 07/880,480, filed May 6, 1992, now abandoned).

BACKGROUND OF THE INVENTION

Cholecystokinins (CCK) and gastrin are structurally-related neuropeptides which exist in gastrointestinal tissue and in the central nervous system (see, V. Mutt, *Gastrointestinal Hormones*, G. B. J. Glass, Ed., Raven Press, N.Y., p. 169 and G. Nisson, p. 127).

Cholecystokinins include CCK-33, a neuropeptide of thirty-three amino acids in its originally isolated form (see, Mutt and Jorpes, *Biochem. J.* 125, 678 (1971)), its carboxyl terminal octapeptide CCK-8 (a naturally-occurring neuropeptide, also, and the minimum fully active sequence), and 39- and 12-amino acid forms, while gastrin occurs in 34-, 17- and 14-amino acid forms, with the minimum active sequence being the C-terminal tetrapeptide Trp-Met-Asp-Phe-$NH_2$, which is the common structural element shared by both CCK and gastrin.

CCK's are believed to be physiological satiety hormones, thereby possibly playing an important role in appetite regulation (G. P. Smith, *Eating and Its Disorders*, A. J. Stunkard and E. Stellar, Eds, Raven Press, New York, 1984, p. 67), as well as also stimulating colonic motility, gall bladder contraction, pancreatic enzyme secretion, and inhibiting gastric emptying. They reportedly coexist with dopamine in certain mid-brain neurons and thus may also play a role in the functioning of dopaminergic systems in the brain, in addition to serving as neurotransmitters in their own right (see: A. J. Prange et al., "Peptides in the Central Nervous System", *Ann. Repts. Med. Chem.* 17, 31, 33 [1982] and references cited therein; J. A. Williams, *Biomed. Res.* 3 107 [1982]; and J. E. Morley, *Life Sci.* 30, 479, (1982)).

The primary role of gastrin, on the other hand, appears to be stimulation of the secretion of water and electrolytes from the stomach, and, as such, it is involved in control of gastric acid and pepsin secretion. Other physiological effects of gastrin include increased mucosal blood flow and increased antral motility, with rat studies having shown that gastrin has a positive trophic effect on the gastric mucosa, as evidenced by increased DNA, RNA and protein synthesis.

Antagonists to CCK and to gastrin have been useful for preventing and treating CCK-related and/or gastrin-related disorders of the gastrointestinal (GI) and central nervous (CNS) systems of animals, especially of humans. Just as there is some overlap in the biological activities of CCK and gastrin, antagonists also tend to have affinity for both receptors. In a practical sense, however, there is enough selectivity to the different receptors that greater activity against specific CCK- or gastrin-related disorders can often also be identified.

Selective CCK antagonists are themselves useful in treating CCK-related disorders of the appetite regulatory systems of animals as well as in potentilting and prolonging opiate-mediated analgesia, thus having utility in the treatment of pain [see P. L. Faris et al., Science 226, 1215 (1984)], while selective gastrin antagonists are useful in the modulation of CNS behavior, as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value. See e.g. U.S. Pat. No. 4,820,834.

Since CCK and gastrin also have trophic effects on certain tumors [K. Okyama, *Hokkaido J. Med. Sci.*, 60, 206–216 (1985)], antagonists of CCK and gastrin are useful in treating these tumors [see, R. D. Beauchamp et al., *Ann. Surg.*, 202,303 (1985)].

Four distinct chemical classes of CCK-receptor antagonists have been reported [R. Freedinger, *Med. Em. Rev.* 9, 271 (1989)). The first class comprises derivatives of cyclic nucleotides, of which dibutyryl cyclic GMP has been shown to be the most potent by detailed structure-function studies (see, N. Barlas et al., *Am. J. Physiol.*, 242, G 161 (1982) and P. Robberecht et al., *Mol., Pharmacol.*, 17, 268 (1980)).

The second class comprises peptide antagonists which are C-terminal fragments and analogs of CCK, of which both shorter (Boc-Met-Asp-Phe-$NH_2$, Met-Asp-Phe-$NH_2$), and longer (Cbz-Tyr($SO_3H$)-Met-Gly-Trp-Met-Asp-$NH_2$) C-terminal fragments of CCK can function as CCK antagonists, according to recent structure-function studies (see, R. T. Jensen et al., *Biochem. Bioshys. Acta.*, 757, 250 (1983), and M. Spanarkel et al., *J. Biol. Chem.*, 258, 6746 (1983)). The latter compound was recently reported to be a partial agonist [see, J. M. Howard et al., *Gastroenterology* 86(5) Part 2, 1118 (1984)].

Then, the third class of CCK-receptor antagonists comprises the amino acid derivatives: proglumide, a derivative of glutaramic acid, and the N-acyl tryptophans including para-chlorobenzoyl-L-tryptophan (benzotript), [see, W. F. Hahne et al., *Proc. Natl. Acad. Sci. U.S.A.*, 78, 6304 (1981), R. T. Jensen et al., *Biochem. Bioshys. Acta.*, 761, 269 (1983)]. All of these compounds, however, are relatively weak antagonists of CCK ($IC_{50}$: generally $10^{-4}M$ [although more potent analogs of proglumide have been recently reported in F. Makovec et al., *Arzneim-Forsch Drug Res.*, 35 (II), 1048 (1985) and in German Patent Application DE 3522506A1], but down to $10^{-6}M$ in the case of peptides), and the peptide CCK-antagonists have substantial stability and absorption problems.

In addition, a fourth class consists of improved CCK-antagonists comprising a nonpeptide of novel structure from fermentation sources (R. S. L. Chang et al., *Science*, 230, 177–179 (1985)] and 3-substituted benzodiazepines based on this structure [published European Patent Applications 167 919, 167 920 and 169 392, B. E. Evans et al, *Proc. Natl. Acad. Sci. U.S.A.*, 83, p. 4918–4922 (1986) and R. S. L. Chang et al, ibid, p. 4923–4926] have also been reported.

No really effective receptor antagonists of the in vivo effects of gastrin have been reported (J. S. Morley, *Gut*

*Pept. Ulcer Proc.*, Hiroshima Symp. 2nd, 1983, p. 1), and very weak in vitro antagonists, such as proglumide and certain peptides have been described [(J. Martinez, J. Med. Chem. 27, 1597 (1984)]. Recently, however, pseudopeptide analogs of tetragastrin have been reported to be more effective gastrin antagonists than previous agents [J. Martinez et al., *J. Med. Chem.*, 28, 1874–1879 (1985)].

The benzodiazepine (BZD) structure class, which has been widely exploited as therapeutic agents, especially as central nervous system (CNS) drugs, such as anxiolytics, and which exhibits strong binding to "benzodiazepine receptors" in vitro, has not in the past been reported to bind to CCK or gastrin receptors. Benzodiazepines have-been shown to antagonize CCK-induced activation of rat hippocampal neurones but this effect is mediated by the benzodiazepine receptor, not the CCK receptor [see J. Bradwejn et al., *Nature*, @2, 363 (1984)]. Benzodiazepines unsubstituted at the 3-position of the seven membered ring have been shown to antagonize the effects of CCK-4 (a CCK analog) (See DeMontigny, C. *Arch. Gen. Psychiatry* 46, 511 (1989)]. Of the reported BZD's, additionally, the large majority do not contain substituents attached to the 3-position of the seven membered ring, as it is well known in the art that 3-substituents result in decreasing benzodiazepine receptor affinity and decreasing anxiolytic activity, especially as these substituents increase in size.

Contrary to these findings, applicants have discovered a class of benzodiazepines with 3-substituents having high CCK and/or gastrin receptor affinity and low benzodiazepine receptor affinity. The compounds of the present invention also provide enhanced aqueous solubility as compared to those of U.S. Pat. No. 4,820,834. The compounds of the invention are useful in the treatment of disorders of gastric secretion, appetite regulation, gastrointestinal motility, pancreatic secretion, and dopaminergic function, as well as in treatment of producing potentiation of morphine and other opiate analgesias. The present compounds also provide improvements in aqueous solubility, receptor selectivity, oral bioavailability, and duration of action.

It is, therefore, an object of this invention to identify substances which more effectively antagonize or inhibit the function of cholecystokinins and gastrin in the treatment of disorders of gastric secretion, appetite regulation, gastrointestinal motility, pancreatic secretion, and dopaminergic function, as well as in treatment or producing potentiation of morphine and other opiate analgesias. It is another object of this invention to develop a method of antagonizing the functions of cholecystokinin and/or gastrin in these disorders. It is also an object of this invention to develop a method of preventing or treating these disorders.

The substituted benzodiazepines of the present invention are also useful for directly inducing analgesia, either opiate mediated or non-opiate mediated. Furthermore, the compounds of the present invention are useful as anesthetic agents involving the loss of pain sensations. It is therefore another object of the present invention to identify substances which more effectively antagonize or inhibit the function of CCK or gastrin for the purpose of effecting analgesia, anesthesia, or loss of pain sensation. Yet another object of the present invention is to develop methods of antagonizing or inhibiting the functions of CCK or gastrin for the purpose of effecting analgesia, anesthesia or loss of pain sensation.

SUMMARY OF THE INVENTION

It has now been found that compounds of Formula I are antagonists of gastrin and cholecystokinin (CCK) and bind to the gastrin and CCK receptors. Pharmaceutical compositions containing effective amounts of these compounds are useful in the treatment and prevention of CCK and/or gastrin-related disorders of gastric secretion, appetite regulation, gastrointestinal motility, pancreatic secretion, and dopaminergic function, as well as in treatment producing potentiation of morphine and other opiate analgesics. The present compounds provide enhanced aqueous solubility.

DETAILED DESCRIPTION OF THE INVENTION

The compounds of formula I are useful in a method of antagonizing the binding of cholecystokinin to cholecystokinin receptors or antagonizing the binding of gastrin to gastrin receptors which comprises contacting said cholecystokinin receptors or said gastrin receptors, respectively, with a compound represented by the formula:

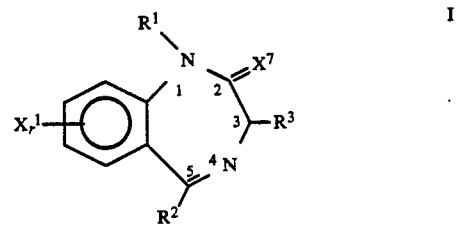

wherein:
R$^1$ is H, C$_1$–C$_6$ linear or branched alkyl, loweralkenyl, lower alkynyl, X$^{12}$COOH, —X$^{12}$COOR$^6$, —X$^{11}$-cycloloweralkyl, —X$^{12}$NR$^4$R$^5$, —X$^{12}$CONR$^4$R$^5$, —X$^{12}$CN, or —X$^{11}$CX$_3^{10}$;

R$^2$ is H, loweralkyl, substituted or unsubstituted phenyl (wherein the substitutents may be 1 or 2 of halo, loweralkyl, loweralkoxy, loweralkythio, carboxyl, carboxyloweralky, nitro, —CF$_3$, or hydroxy), 2-,3-, or 4-pyridyl;

R$^3$ is

NH(CH$_2$)$_{2—3}$NHCOR$^7$,

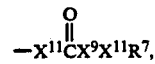

—X$^{11}$NR$^{18}$SO$_2$(CH$_2$)$_q$R$^7$;

R$^4$ and R$^5$ are independently H or R$^6$ or in combination with the N of the NR$^4$R$^5$ group form an unsubstituted or mono or disubstituted, saturated or unsaturated, 4–7 membered heterocyclic ring, or benzofused, 4–7 membered heterocyclic ring wherein said heterocyclic ring or said benzofused heterocyclic ring may contain a second heteroatom selected from O and NCH₃ and the substituents(s) is/are independently selected from $C_1$-$C_4$alkyl;

$R^6$ is loweralkyl, cycloloweralkyl, substituted or unsubstituted phenyl, or substituted or unsubstituted phenylloweralkyl wherein the phenyl or phenylloweralkyl substituents may be 1 or 2 of halo, loweralkyl, loweralkoxy, nitro, or $CF_3$;

$R^7$ is

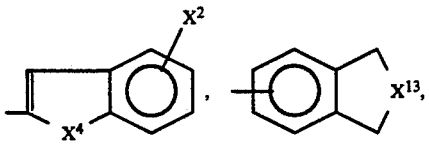

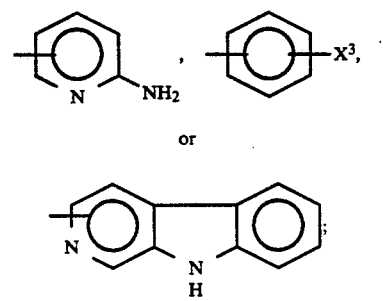

$R^8$ is H, loweralkyl, cycloloweralkyl, —$X^{13}$CONH₂, —$X^{13}$COOR⁶, —$X^{13}$COOH, —$X^{13}$-cycloloweralkyl, or —$X^{13}$NR⁴R⁵, $R^{15}$ is H, or loweralkyl, $R^{18}$ is H or loweralkyl;

n is 1–6, q is 0–4;

r is 1 or 2;

$X^1$ is H,—$NO_2$, $CF_3$, CN, OH, loweralkyl, halo, loweralkylthio, loweralkoxy, —$X^{11}$COOR⁶, $X^{11}$COOH, or —$X^{11}$NR⁴R⁵, $X^2$ is H or $X^3$, with the proviso that when $X^2$ is H, then $X^4$ is NX⁵COOH or NX⁵COOR⁶ wherein $X^5$ is a linear alkyl chain of 2 to 6 carbon atoms, any carbon atom of which may be additionally substituted with a linear or branched alkyl group of 1 to 3 carbon atoms;

$X^3$ is O(CH₂)ₙCOOR⁶, O(CH₂)ₙCOOH, (CH₂)ₙCOOR⁶, (CH₂)ₙCOOH, COOR⁶, or $X^{12}$OR⁶;

$X^4$ is S, O, CH₂, or NR⁸;

$X^7$ is O, S, HH, or NR¹⁵ with the proviso that $X^7$ can be NR¹⁵ only when $R^1$ is not H;

$X^8$ is H, loweralkyl;

$X^9$ and $X_a^9$ are independently NR¹⁸ or O;

$X^{10}$ is F, Cl, or Br;

$X^{11}$ is absent or $C_{1-4}$ linear or branched alkyl with two points of connection;

$X^{12}$ is $C_{1-4}$ linear or branched alkyidene;

$X^{13}$ is $C_{1-4}$ linear or branched alkyl with two points of connection;

or pharmaceutically acceptable salts thereof.

One embodiment of the present invention encompasses compounds of formula 1, wherein:

$R^1$ is H, $C_1$-$C_6$ linear or branched alkyl, —$X^{12}$COOR⁶, —$X^{11}$-cycloloweralkyl, $X^{12}$NR⁴R⁵, —$X^{12}$CONR⁴R⁵, or $X^{12}$COOH;

$R^2$ is substituted or unsubstituted phenyl (wherein the substitutents may be 1 or 2 of halo, loweralkyl, loweralkoxy, loweralkylthio, carboxyl, carboxyloweralkyl, nitro, —$CF_3$ or hydroxy), 2-,3-, or 4-pyridyl;

$R^3$ is

—NH(CH₂)₂₋₃NHCOR⁷, or

$R^4$ and $R^5$ are independently H or R⁶ or in combination with the N or the NR⁴R⁵ group form an unsubstituted or mono or disubstituted, saturated or unsaturated, 4–7 membered heterocyclic ring, or benzofused 4–7 membered heterocyclic ring wherein said heterocyclic ring or said benofused heterocyclic ring may contain a second heteroatom selected from O and NCH₃ and the substituents(s) is/are independently selected from $C_1$-$C_4$ alkyl;

$R^6$ is $C_{1-4}$ straight or branched-chain alkyl or $C_3$-$C_6$ cycloalkyl;

$R^7$ is

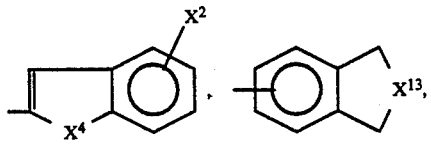

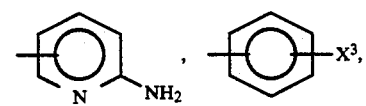

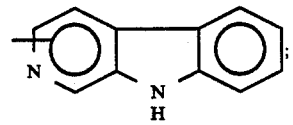

$R^8$ is H, loweralkyl, cycloloweralkyl, $X^{13}$COOR⁶, $X^{13}$COOH, or $X^{13}$NR⁴R⁵;

$R^{18}$ is H or loweralkyl;

n is 1–3;

q is 0–3;

r is 1 or 2;

$X^1$ is H, —$NO_2$, $CF_3$, CN, loweralkyl, halo, loweralkylthio —$X^{11}$COOR⁶, $X^{11}$COOH, or $X^{11}$NR⁴R⁵;

$X^2$ is H or $X^3$ with the proviso that when $X^2$ is H, then $X^4$ is NX⁵COOH or NX⁵COOR⁶ wherein $X^5$ is a linear alkyl chain of 2 to 4 carbon atoms, any carbon atom of which may be additionally substituted with a linear or branched alkyl group of 1 to 3 carbon atoms;

$X^3$ is O(CH₂)ₙCOOR⁶, O(CH₂)ₙCOOH, (CH₂)ₙCOOR⁶, (CH₂)ₙCOOH, or COOR⁶;

$X^4$ is S, O, or NR⁸;

$X^7$ is O;

$X^9$ and $X_a^9$ are independently NR¹⁸, or O;

$X^{11}$ is absent or $C_{1-4}$ linear alkyl;
$X^{12}$ is $C_{1-4}$ linear or branched alkylidene;
$X^{13}$ is $C_{1-4}$ linear or branched alkyl;
or pharmaceutically acceptable salt thereof.

As used herein, the definition of each substituent e.g., $R^7$, loweralkyl, etc., when it occurs more than once in any structure, is intended to be independent of its definition elsewhere in the s&me structure. Alkylidene is an alkyl group with two hydrogens abstracted from the same carbon atoms.

As used herein, halo is F, Cl, Br or I; alkyl and loweralkyl are each, unless otherwise indicated, 1-7 carbon straight or branched chain saturated alkyl having one or sometimes two hydrogens abstracted, and includes methyl, ethyl, propyl, isopropyl, butyl, isobutyl, and t-butyl, pentyl, hexyl, and heptyl; in loweralkoxy and loweralkylthio, the alkyl portion is loweralkyl as previously defined; cycloloweralkyl is cycloalkyl of 3-7 carbons; loweralkenyl is 1-5 carbon straight or branched chain alkenyl; acyl is formyl, acetyl, propionyl, benzoyl or butyryl; loweralkynyl is 1-5 carbon straight or branched chain alkynyl.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The compounds of formula (I) antagonise CCK and-/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression such as depression resulting from organic disease secondary to stress associated with personal loss or idiopathic depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further be useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous glial and neuronal cells. Examples of such adenocarcinomas and tumours include, but are not limited to, tumours of the lower esophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-pontocerebellar atrophy, anoxia such as from drowning, spinal cord and head injury, and poisoning by neurotoxins, including envirorunental neurotoxins.

The compounds of formula (I) may further be used to induce miosis for therapeutic purposes after certain types of examination and intraocular surgery. An example of intraocular surgery would include cateract surgery with implantation of an artifical lens. The CCK antagonist compounds of this invention can be used to prevent miosis occuring in association with iritis, ureitis and trauma.

The present invention also encompasser a pharmaceutical composition useful in the treatment of these disorders or other disorders involving CCK and/or gastrin antagonism, comprising an effective amount of a CCK and/or gastrin antagonist of formula I, with or without pharmaceutically-acceptable carriers or diluents. In addition, the present invention encompasses a pharmaceutical composition useful for directly inducing analgesia, anesthesia or loss of the sensation of pain.

The compounds of Formula I thereof, may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of CCK or gastrin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.05 µg/kg to about 50 mg/kg of body weight, and preferably, of from 0.5 µg/kg to about 20 mg/kg of body weight, administered in single or divided doses. In some cases, however, it may be necessary to use dosages outside these limits.

In the treatment of irritable bowel syndrome, for instance, 0.1 to 10 mg/kg or a CCK antagonist might be administered orally (p.o.), divided into two doses per day (b.i.d.). In treating delayed gastric emptying, the dosage range would probably be the same, although the drug might be administered either intravenously (I.V.) or orally, with the I.V. dose probably tending to be slightly lower due to better availability. Acute pancreatitis might be treated preferentially in an I.V. form, whereas spasm and/or reflex esophageal, chronic pancreatitis, post vagotomy diarrhea, anorexia or pain associated with biliary dyskinesia might indicate p.o. form administration.

In the use of a gastrin antagonist as a tumor palliative for gastrointestinal neoplasms with gastrin receptors, as a modulator of central nervous system activity, treatment of Zollinger-Ellison syndrome, or in the treatment of peptic ulcer disease, a dosage of 0.1 to 10 mg/kg administered one-to-four times daily might be indicated.

Because these compounds antagonize the function of CCK in animals, they may also be used as feed additives to increase the food intake of animals in daily dosage of approximately 0.05 to 100 µg/kg of body weight.

The compounds of Formula I are prepared according to the schemes and descriptions of U.S. Pat. No. 4,820,834 herein incorporated by reference for these purposes. One preferred synthetic scheme is Scheme IVa involving nitrosation, reduction and acylation, according to U.S. Pat. No. 4,820,834. See also Examples 1–20 below.

1. CCK Receptor Binding (Pancreas)

CCK-33 was radiolabeled with $^{125}$I-Bolton Hunter reagent (2000 Ci/mmole) as described by Sankara et al. (J. Biol. Chem. 254: 9349–9351, 1979). Receptor binding was performed according to Innis and Snyder (Proc. Natl. Acad. Sci. 77, 6917–6921, 1980) with the minor modification of adding the additional protease inhibitors, phenylmethane sulfonyl fluoride and o-phenanthroline. The latter two compounds have no effect on the $^{125}$-CCK receptor binding assay.

Male Sprague-Dawley rats (200–350 g) were sacrificed by decapitation. The whole pancreas was dissected free of fat tissue and was homogenized in 20 volumes of ice-cold 50 mM, Tris HCl (pH 7.7 at 25° C.) with a Brinkmann Polytron PT 10. The homogenates were centrifuged at 48,000 g for 10 min. Pellets were resuspended in Tris Buffer, centrifuged as above and resuspended in 200 volumes of binding assay buffer (50 mM Tris HCl, pH 7.7 at 25° C., 5 mM dithiothrietol, 0.1 mM bacitracin, 1.2 mM phenylmethane sulfonyl fluoride and 0.5 mM o-phenanthroline). For the binding assay, 25 µl of buffer (for total binding) or unlabeled CCK-8 sulfate to give a final concentration of 1 µM (for nonspecific binding) or the compounds of Formula I (for determination of inhibition of $^{125}$I-CCK binding) and 25 µl of $^{125}$-CCK-33 (30,000–40,000 cpm) were added to 450 µl of the membrane suspensions in microfuge tubes. All assays were run in duplicate or triplicate. The reaction mixtures were incubated at 37° C. for 30 minutes and centrifuged in a Beckman Microfuge (4 minutes) immediately after adding 1 ml of ice-cold incubation buffer. The supernatant was aspirated and discarded, pellets were counted with a Beckman gamma 5000. For Scatchard analysis (Ann. N.Y. Acad. Sci. 51: 660, 1949), $^{125}$-CCK-33 was progressively diluted with increasing concentrations of CCK-33.

2. CCK Receptor Binding (Brain)

CCK-33 was radiolabeled and the binding was performed according to the description for the pancreas method with modifications according to Saito et al., J. Neurochem. 37:483–490, 1981.

Male Hartley guinea pigs (300–500 g) were sacrificed by decapitation and the brains were removed and placed in ice-cold 50 mM, Tris HCl plus 7.58 g/l Trizma-7.4 (pH 7.4 at 25° C.). Cerebral cortex was dissected and used as a receptor source. Each gram of fresh guinea pig brain tissue was homogenized in 10 ml of Tris/Trizma buffer with a Brinkman polytron PT-10. The homogenates were centrifuged at 42,000 g for 15 minutes. Pellets were resuspended in Tris Buffer, centrifuged as above and resuspended in 200 volumes of binding assay buffer (10 mM N-2-hydroxyethyl-piperazine-N'-2-ethane sulfonic acid (HEPES), 5 mM MgCl$_2$, 0.25 mg/ml bacitracin, 1 mM ethylene glycol-bis-($\beta$-aminoethylether-N,N'-tetraadetic acid) (EGTA), and 0.4% bovine serum albumin (BSA)). For the binding assay, 25 µl of buffer (for total binding) or unlabeled CCK-8 sulfate to give a final concentration of 1 µm (for nonspecific binding) or the compounds of Formula I (for determination of inhibition of $^{125}$I-CCK binding) and 25 µl of $^{125}$I-CCK-33 (30,000–40,000 cpm) were added to 450 µl of the membrane suspensions in microfuge tubes. All assays were run in duplicate or triplicate. The reaction mixtures were incubated at 25° C. for 2 hours and centrifuged in a Beckman Microfuge (4 minutes) immediately after adding 1 ml of ice-cold incubation buffer. The supernatant was aspirated and discarded, pellets were counted with a Beckman gamma 5000.

The compounds of Formula I can be determined to be competitive antagonists of CCK according to the following assays.

3. Isolated guinea pig gall bladder

Male Hartley guinea pigs (400–600 g) are sacrificed by decapitation. The whole gall bladder is dissected free from adjacent tissues and cut into two equal halves. The gall bladder strips are suspended along the axis of the bile duct in a 5 ml organ bath under 1 g tension. The organ bath contains a Kreb's bicarbonate solution (NaCl 118 mM, KCl 4.75 mM, CaCl 2.54 mM, $KH_2PO_4$ 1.19 mM, Mg $SO_4$ 1.2 mM, $NaHCO_3$ 25 mM and dextrose 11 mM) maintained at 32° C. and bubbled with 95% $O_2$ and 5% $CO_2$. Isometric contractions are recorded using Statham (60 g; 0.12 mm) strain gauges and a Hewlett-Packard (77588) recorder. The tissues are washed every 10 minutes for 1 hour to obtain equilibrium prior to the beginning of the study. CCK-8 is added cumulatively to the baths and $EC_{50}$'s determined using regression analysis. After washout (every 10 minutes for 1 hour), the compound of Formula I is added at least 5 minutes before the addition of CCk-8 and the $EC_{50}$ of CCK-8 in the presence of the compound of Formula I similarly determined.

4. Isolated longitudinal muscle of guinea pig ileum

Longitudinal muscle strips with attached nerve plexus are prepared as described in *Brit. J. Pharmac.* 21: ; 356–363, 1964; *J. Physiol.* 194: 13–33, 1969. Male Hartley guinea pigs are decapitated and the ileum removed (10 cm of the terminal ileum is discarded and the adjacent 20 cm piece used). A piece (10 cm) of the ileum is stretched on a glass pipette. Using a cotton applicator to stroke tangentially away from the mesentery attachment at one end, the longitudinal muscle is separated from the underlying circular muscle. The longitudinal muscle is then tied to a thread and by gently pulling, stripped away from the entire muscle. A piece of approximately 2 cm is suspended in 5 ml organ bath containing Krebs solution and bubbled with 95% $O_2$ and 5% $CO_2$ at 37° C. under 0.5 g tension. CCK-8 is added cumulatively to the baths and $EC_{50}$ values in the presence and absence of compounds of Formula I determined as described in the gall bladder protocol (above).

5. Gastrin Antagonism

Gastrin antagonist activity of compounds of Formula I is determined using the following assay.

A. Gastrin Receptor Binding in Guinea Pig Gastric Glands

Preparation of guinea pig gastric mucosal glands

Guinea pig gastric mucosal glands were prepared by the procedure of Berglingh and Obrink Acta Physiol. Scand. 96: 150 (1976) with a slight modification according to Praissman et al. C. J. Receptor Res. 3: (1983). Gastric mucosa from guinea pigs (300–500 g body weight, male Hartley) were washed thoroughly and minced with fine scissors in standard buffer consisting of the following: 130 mM NaCl, 12 mM $NaHCO_3$, 3 mM $NaH_2PO_4$, 3 mM $Na_2HPO_4$, 3 mM $K_2HPO_4$, 2 mM $MgSO_4$, 1 mM $CaCl_2$, 5 mM glucose and 4 mM L-glutamine, 25 mM HEPES at pH 7.4. The minced tissues were washed and then incubated in a 37° C. shaker bath for 40 minutes with the buffer containing 0.1% collagenase and 0.1% BSA and bubbled with 95% $O_2$ and 5% $CO_2$. The tissues were passed twice through a 5 ml glass syringe to liberate the gastric glands, and then filtered through 200 mesh nylon. The filtered glands were centrifuged at 270 g for 5 minutes and washed twice by resuspension and centrifugation.

B. Binding studies

The washed guinea pig gastric glands prepared as above were resuspended in 25 ml of standard buffer containing 0.25 mg/ml of bacitracin. For binding studies, to 220 μl of gastric glands in triplicate tubes, 10 μl of buffer (for total binding) or gastrin (1 μM final concentration, for nonspecific binding) or test compound and 10 μl of $^{125}$I-gastrin (NEN, 2200 Ci/mmole, 25 pM final) or $^3$H-pentagastrin (NEN 22 Ci/mmole, 1 nM final) were added. The tubes were aerated with 95% $O_2$ and 5% $CO_2$ and capped. The reaction mixtures after incubation at 25° C. for 30 minutes were filtered under reduced pressure on glass G/F B filters (Whatman) and immediately washed further with 4×4 ml of standard buffer containing 0.1% BSA. The radioactivity on the filters was measured using a Beckman gamma 5500 for $^{125}$I-gastrin or liquid scintillation counting for $^3$H-pentagastrin.

In Vitro Results

Effect of The Compounds of Formula I on $^{125}$-CCK-33 receptor binding

The preferred compounds of Formula I are those which inhibited specific $^{125}$I-CCK-33 binding in a concentration dependent manner.

Scatchard analysis of specific $^{125}$I-CCK-33 receptor binding in the absence and presence of the compounds of Formula I indicated the compound of Formula I competitively inhibited specific $^{125}$I-CCK-33 receptor binding since it increased the $K_D$ (dissociation constant) without affecting the $B_{max}$ (maximum receptor number). A $K_i$ value (dissociation constant of inhibitor) of the compounds of Formula I was estimated, The data of Table I were obtained for compounds of Formula I.

TABLE I

CCK RECEPTOR BINDING RESULTS $IC_{50}$ (μM)

| Compound of EX # | $^{125}$I-CCK Pancreas | $^{125}$I-CCK Brain | $^{125}$I-Gastrin Gastric Glands |
|---|---|---|---|
| 5 | 0.28 | 0.002 | 0.0011 |
| 6 | 0.00013 | 0.1290 | 0.07000 |
| 7 | 0.00010 | 0.2300 | 0.24000 |
| 9 | 0.04900 | 0.0039 | 0.00900 |
| 10 | 0.04900 | 0.0039 | 0.00900 |
| 12 | 0.00240 | 0.1600 | 0.24000 |
| 13 | 0.01400 | 0.0710 | 6.40000 |
| 14 | 2.70000 | 0.0110 | 0.40000 |
| 15 | 0.00330 | 0.9100 | |
| 16 | 0.02300 | 0.1600 | |
| 17 | 0.06900 | 0.0120 | 0.00380 |
| 18 | 2.6 | 0.024 | 0.01 |
| 19 | 0.02 | 0.026 | 0.018 |

EXAMPLE 1

1,3-Dihydro-1-methyl-3-oximino-5-phenyl(-2H-1,4-benzodiazepin-2-one

To a suspension of potassium tert-butoxide (24.9 g, 222 mmole) in 600 ml of dry tetrahydrofuran was added 200 ml of dry tert-butylalcohol at −20° C. under nitrogen. To this solution was then added via addition funnel 1,3-dihydro-1-methyl-5-phenyl-2H-1,4-benzodiazepin-2-one (25 g, 99.9 mmole) in 260 ml of tetrahydrofuran. The resulting wine colored solution was stirred for 2 hours at −20° C. and treated with 17.4 ml (130 mmole) of isoamyl nitrite. The reaction mixture was warmed to 0° C. over 15 minutes and quenched with the addition of 60 ml of cold water and 20 ml of glacial acetic acid. All solvents were removed under reduced pressure and the residue was partitioned between ethyl acetate (600 ml) and brine (100 ml). The phases were separated and the organic extracts were dried ($Na_2SO_4$) and concentrated. The resulting semi-solid was triturated with ether to give 21 g of off-white solid. m.p. 234°–235° C.; $R_f$=0.15 (ethyl acetate-hexane, 1:1); $R_f$=0.28 chloroform-ethanol, 95:5);

ir(KBr, partial): 3300, 1650, 1595, 1320, 1205, 1030, 975 cm$^{-1}$.

MS (14 ev.): 279 (M+), 262, 249, 236, 222.

$^1$HNMR (CDCl$_3$): confirms structure assignment.

Elemental Analysis Calc'd for $C_{16}H_{13}N_3O_2$: C, 4.69; E, 68.81; N, 15.04. Found: C, 4.62; H, 68.67; N, 15.08.

EXAMPLE 2

3(R,S)-Amino-1,3-dihydro-1-methyl-5-phenyl-2H-1,4-benzodiazepin-2-one

A solution of 150 ml of methanol containing 5 g (17.9 mmole) of 1,3-dihydro-1-methyl-3-oximino-5-phenyl-1,4-benzodiazepin-2-one was treated with a slurry of active Raney-nickel catalyst[1] in ethanol (10 g wet weight). The resulting suspension was hydrogenated on a Parr apparatus at 60 psi and 23° C. for 30 hours. The catalyst was removed by filtration and the filtrate was concentrated to afford the title compound in 95% yield.
[1] Raney-Nickel catalyst was prepared according to Fieser & Fieser, Reagents for Organic Synthesis, Vol. I, John Wiley & Sons, Inc., New York 1967, p. 729.

$R_f$=0.23 (chloroform-ethanol, 95:5), $R_f$=0.23 (chloroform-methanol-acetic acid-water, 90:10:1:1)

$^1$HNMR (CDCl$_3$): spectrum confirms structure assignment.

EXAMPLE 3

3(S)-(−)-1,3-Dihydro-3-(2-indolecarbonylamino)-1-methyl-5-phenyl-2H-1,4-benzodiazepin-2-one 3(S)-(−)-3-Amino-1,3-dihydro-1-methyl-5-phenyl-2H-1,4-benzodiazepin-2-one (595 mg, 2.24 mmole) was dissolved in CH$_2$Cl$_2$ (15 ml) and treated with 2-indolecarbonyl chloride (403 mg, 2.24 mmole) followed by triethylamine (227 mg, 2.24 mmole). The mixture was stirred at room temperature for 30 minutes and concentrated in vacuo. The residue was chromatographed on silica gel (5% Et$_2$O/CH$_2$Cl$_2$) and the combined product fractions evaporated to dryness in vacuo. Three times, Et$_2$O (15 ml) was added and evaporated in vacuo to give the title compound: (m.p. 168°–185° C.).

TLC: Silica gel (6% Et$_2$O/CH$_2$Cl$_2$), $R_f$=0.23
NMR: Consistent with structure
HPLC: Greater than 99% pure.
M.S.: Molecular ion at m/e=408
$[\alpha]_D^{25}$ − −103° (0.0078 g/ml CH$_2$Cl$_2$)
Anal. calc'd for $C_{25}H_{20}N_4O_2$: C, 73.51; H, 4.94; N, 13.72; Found: C, 73.38; H, 4.80; N, 13.66.

EXAMPLE 4

3(RS)-(Boc-L-tryptophanyl)amino-1,3-dihydro-5-phenyl-2H-1,4-benzodiazepin-2-one 3-(RS)-Amino-1,3-dihydro-5-phenyl-2H-1,4-benzodiazepin-2-one (0.1 g, 0.4 mmol), BOC-L-tryptophan (0.12 g, 0.4 mmol), and DCC (0.4 ml of a 1M solution in CH$_2$Cl$_2$, 0.4 mmol) were combined in 2 ml of THF to which were added 2 ml of DMF and 2 ml of CH$_2$Cl$_2$. The mixture was treated with triethylamine (0.11 ml), stoppered, and stirred at room temperature for four days. The mixture was treated with citric acid solution (10%, 3 ml) and CH$_2$Cl$_2$ (5 ml), shaken and separated. The aqueous phase was extracted with CH$_2$Cl$_2$ (2×5 ml). The combined organic layers were washed with citric acid (10%, 2×5 ml), sodium bicarbonate (10%, 2×5 ml), and H$_2$O (10 ml), dried over sodium sulfate, filtered, and evaporated to dryness in vacuo. The residue was chromatographed on silica gel (1:1 (v/v) Et$_2$O/CH$_2$Cl$_2$) and the combined product fractions evaporated to dryness in vacuo. The residue was triturated with petroleum ether and the solid dried in vacuo at 70°: (m.p. 173°–177° C.

TLC: Single spot ($R_f$=0.56, silica gel plate, 10% (v/v) CH$_3$OH in CH$_2$Cl$_2$).

NMR: The spectrum was consistent with the title structure and verified the presence of two diastereomers.

HPLC: Greater than 99.7% pure (36% and 63.7%).
MS (FAB): a molecular ion at m/e=537.
Anal. calc'd for $C_{31}H_{31}N_5O_4$: C, 69.25; H, 5.81; N, 13.03; Found: C, 69.48; H, 6.18; N, 12.96.

EXAMPLE 5

(R)-N-(2,3-Dihydro-1-methyl-2-oxo-5-phenyl-1H-1,4-benzodiazepin-3-yl)-N'-(3-methylphenyl)-urea Equimolar amounts of 3(R)-amino-1,3-dihydro-1-methyl-5-phenyl-2H-1,4-benzodiazepin-2-one and 3-methylphenylisocyanate were mixed in 8 ml of dry tetrahydrofuran at room temperature. The reaction mixture was allowed to stand for 8 hours and was then filtered. The collected solids were washed with tetrahydrofuran and dried in vacuo over P$_2$O$_5$ to give analytical product: m.p. 208°–210° C.

NMR: Confirms structure assignment of product.
HPLC: Greater than 99% pure.
MS: Molecular ion at m/e=399 (M+H) (FAB).
Anal. Calc'd for $C_{24}H_{22}N_4O_2$: C, 72.34; H, 5.56; N, 14.06. Found: C, 72.12; H, 5.84; N, 14.04.

EXAMPLE 6

3(S)-3-(2-(N-carboxymethylindole)carbonylamino)-1,3-dihydro-1-methyl-5-phenyl-2H-1,4-benzodiazepin-2-one Sodium hydride (0.034 g, 0.71 mmole of a 50% dispersion in mineral oil) and 3(S)-(−)-1,3-Dihydro-3-(2-indolecarbonylamino)-1-methyl-5-phenyl-2H-1,4-benzodiazepin-2-one (0.28 g, 0.69 mmole) were combined in dry, degassed DMF (5 ml) and stirred in an ice bath for 40 minutes. Ethyl bromoacetate (0.077 ml, 0.115 g, 0.69 mmole) was added in one portion, and the mixture stirred one hour at room temperature. The DMF was removed in vacuo, and the residue treated with cold, aqueous sodium bicarbonate solution and extracted with ethyl acetate. The ethyl acetate fractions were combined, washed with water, dried over sodium sulfate, filtered, and evaporated to dryness in vacuo. The residue was chromatographed on silica gel eluted with 7% ether in CH$_2$Cl$_2$. The product fractions were combined and evaporated to dryness in vacuo. The residue (0.25 g, 0.53 mmole) W&s stirred in CH$_3$OH (5 ml) and treated with aqueous sodium hydroxide (0.7 ml of a 1N solution; 0.7 mmole). The mixture was stirred overnight at room temperature, then acidified with 1N HCl and extracted with ethyl acetate. The ethyl acetate fractions were combined, dried over sodium sulfate, filtered, and evaporated to dryness in vacuo. The residue was crystallized from a mixture of acetone, ether, and petroleum ether to give the title compound: (m.p. 165°–195° C. (indistinct)).

TLC: Silica gel (90:10:1:1, $CH_2Cl_2:CH_3OH:HOAc:H_2O$), $R_f=0.52$
NMR: Consistent with structure
HPLC: Greater than 97% pure
M.S.: Molecular ion at M+H=467 (FAB).
Anal. calc'd for $C_{27}H_{22}N_4O_4 \cdot 0.15\ C_4H_{10}O \cdot 0.45\ H_2O$ C, 68.24; H, 5.06; N, 11.54; Found: C, 68.21; H, 4.85; N, 11.47.

EXAMPLE 7

(S)-4-[-2-(((2,3-Dihydro-1-methyl-2-oxo-5-phenyl-1H-1,4-benzodiazepin-3-yl)amino)carbonyl)-1H-indolyl-1]-butanoic acid Sodium hydride (0.1 g, 2.5 mmole of a 60% dispersion in mineral oil) and 3(S)-(−)-1,3-dihydro-3-(2-indolecarbonylamino)-1-methyl-5-phenyl-2H-1,4-benzodiazepin-2-one (1.0 g, 2.45 mmole) were combined in dry, degassed DMF (10 ml) and stirred in an ice bath for 40 minutes. Ethyl-4-bromobutyrate (0.52 g, 2.7 mmole) was added in one portion, and the mixture stirred three hours at room temperature. The DMF was removed in vacuo, and the residue was treated with $CH_3OH$ (350 ml) and aqueous 1N NaOH (10 ml) and stirred at room temperature for three days. The mixture was evaporated to dryness in vacuo, and the residue was treated with aqueous sodium bicarbonate solution and extracted with ethyl acetate. The aqueous fraction was made acidic with 1N HCl and extracted with ethyl acetate. The ethyl acetate layer was dried over sodium sulfate and evaporated to dryness in vacuo. The residue was chromatographed on silica gel (7% $Et_2O/CH_2Cl_2$ followed by 540:10:1:1, $CH_2Cl_2: CH_3OH:HOAc:H_2O$, and the product fractions evaporated to dryness in vacuo. The residue was crystallized from ether to give the title compound: (m.p. 192°–195° C.).

TLC: Silica gel (90:10:1:1, $CH_2Cl_2:CH_3OH:HOAc:H_2O$), $R_f=0.23$
NMR: Consistent with structure
HPLC: Greater than 97% pure
M.S.: Molecular ion at M+H=495 (FAB)
Anal. calc'd for $C_{29}H_{26}N_4O_4$ C, 70.43; H, 5.30; N, 11.33; Found: C, 70.14; H, 5.42; N, 11.36.

EXAMPLE 8

(RS)-1,3-Dihydro-1-methyl-3-(p-nitrophenyloxycarbonyl)amino-5-phenyl-2H-1,4-benzodiazepin-2-one 3-(RS)-Amino-1,3-dihydro-1-methyl-5-phenyl-2H-1,4-benzodiazepin-2-one (15.1 g, 57 mmole) was dissolved in THF (150 ml), cooled in an-ice bath, and treated with triethylamine (7.93 ml). A solution of p-nitrophenylchloroformate (11.45 g, 57 mmole) in THF (70 ml) was added dropwise. An additional 1 ml of triethylamine and a solution of 2.0 g of p-nitrophenylchloroformate in THF were added. After stirring one hour, the mixture was filtered and evaporated to dryness in vacuo. Ether was added and the mixture stirred one hour at room temperature and filtered. The solid was washed twice with ether and dried to give the title compound.

EXAMPLE 9

(RS)-3-((((2,3-Dihydro-1-methyl-2-oxo-5-phenyl-1H-1,4-benzodiazepin-3-yl)amino)carbonyl)amino)benzoic acid, also known as
(RS)-N-(2,3-dihydro-1-methyl-2-oxo-5-phenyl-1H-1,4-benzodiazepin-3-yl)-N'-(3-carboxyphenyl)-urea (RS)-1,3-Dihydro-1-methyl-3-(p-nitrophenyloxycarbonyl)amino-5-phenyl-2H-1,4-benzodiazepin-2-one (5.03 g, 11.2 mmole) and m-aminobenzoic acid (2.4 g, 17.5 mmole) were combined in DMF (120 ml), treated with triethylamine (4.2 ml), and stirred in an oil bath thermostatted at 45° for 18 hours. The DMF was removed in vacuo and the residue was dissolved in boiling methanol. The crystallized product was recrystallized from hot methanol: (m.p. 175°–180° C.).

TLC: Silica gel (90:10:1:1, $CH_2Cl_2:CH_3OH:HOAc:H_2O$), $R_f=0.5$
NMR: Consistent with title structure
HPLC: Greater than 97.8% pure
M.S.: M+H at m/e=429 (FAB)
Anal. calc'd for $C_{24}H_{20}N_4O_4 \cdot 1.15H_2O$ C, 64.17; H, 5.00; N, 12.47; Found: C, 64.20; H, 5.20; N, 12.60.

EXAMPLE 10

(R)-3-((((2,3-Dihydro-1-methyl-2-oxo-5-phenyl-1H-1,4-benzodiazepin-3-yl)amino)carbonyl)amino)benzoic acid Benzyl alcohol (10 g, 92.6 mmole) was treated with a solution of m-nitrobenzoyl chloride (17.5 g, 94.5 mmole) in ether (50 ml) added dropwise. The mixture was stirred at room temperature for eighteen hours, then washed twice with aqueous sodium bicarbonate, dried over sodium sulfate, and filtered. The filtrate was evaporated to dryness in vacuo and the residue chromatographed on silica gel eluted with 1:1 $CH_2Cl_2$:hexane. The product fractions were combined and evaporated to dryness in vacuo. A portion (5.2 g, 20.2 mmole) of the resulting benzyl m-nitrobenzoate was dissolved in ethanol and hydrogenated over platinum oxide (70 mg) at 50 psi of $H_2$. The resulting mixture was filtered and evaporated to dryness in vacuo to give benzyl m-aminobenzoate.

(R)-1,3-Dihydro-1-methyl-3-(p-nitrophenyloxycarbonyl)amino-5-phenyl-2H-1,4-benzodiazepin-2-one was prepared using the procedure of Example 8 wherein 3-(R)-Amino-1,3-dihydro-1-methyl-5-phenyl-2H-1,4-benzodiazepin-2-one was employed in place of the (RS) compound.

To benzyl m-aminobenzoate (0.25 g, 1.10 mmole) in DMF (17 ml) was added triethylamine (0.23 ml) followed by a solution of (R)-1,3-dihydro-1-methyl-3-(p-nitrophenyloxycarbonyl)amino-5-phenyl-2H-1,4-benzodiazepin-2-one (0.469 g, 1.09 mmole) in DMF (23 ml) containing triethylamine (0.23 ml). The mixture was stirred at room temperature for one hour, then treated with water, made acidic with 1N HCl, and extracted with ethyl acetate. The ethyl acetate layers were combined, washed with aqueous sodium bicarbonate, dried over sodium sulfate, filtered, and evaporated to dryness in vacuo. The residue was chromatographed on silica gel eluted with 500 ml each of 5%, 6%, 7%, 9%, 10%, and 12% ether in $CH_2Cl_2$. The product fractions were combined and evaporated to dryness in vacuo. A portion of the residue (81.2 mg, 0.086 mmole) was dissolved in ethanol (70 ml) and hydrogenated over palladium/charcoal (20 mg) at 50 psi of $H_2$. The mixture wag filtered and evaporated to dryness in vacuo to provide the title compound.

TLC: Silica gel (90:10:1:1, $CH_2Cl_2$:$CH_3OH$:HOAc:$H_2O$) identical to material prepared as in Example 9.

EXAMPLE 11

3-(RS)-Amino-1,3-dihydro-1-(2-hydroxyethyl)-5-phenyl-2H-1,4-benzodiazepin-2-one 1,3-Dihydro-5-phenyl-3(R,S)-[(benzyloxycarbonyl)amino]-2H-1,4-benzodiazepin-2-one[1] (0.25 g, 0.65 mmole) was dissolved in DMF (5 ml) stirred in an ice bath. The solution was treated with sodium hydride (32.7 mg, 0.681 mmole of a 50% dispersion in mineral oil) and the mixture stirred for forty minutes in the cold. Oxirane gas was bubbled into the mixture for five minutes, and the resulting mixture heated on a steam bath for one hour. The DMF was removed in vacuo. The residue was treated with water and extracted with ethyl acetate. The ethyl acetate layers were combined, washed with water, dried over sodium sulfate, filtered, and evaporated to dryness in vacuo. The residue was chromatographed on silica gel eluted with 35% ethyl acetate in methylene chloride. The combined product fractions were evaporated to dryness in vacuo. The residue was dissolved in $CH_2Cl_2$, cooled in an ice bath, and saturated with HBr gas. The mixture was evaporated to dryness in vacuo, treated with a minimum volume of water and extracted repeatedly with ethyl acetate. The ethyl acetate layers were combined, dried over sodium sulfate, filtered, and evaporated to dryness in vacuo to give the title compound.

[1]Bock, M. G., et al., J. Org. Chem., 52, 3232 (1987).

EXAMPLE 12

(RS)-N-(2,3-Dihydro-1-(2-hydroxyethyl)-2-oxo-5-phenyl-1H-1,4-benzodiazepin-3-yl)-1H-indole-2-carboxamide 3-(RS)-Amino-1,3-dihydro-1-(2-hydroxyethyl)-5-phenyl-2H-1,4-benzodiazepin-2-one (69.0 mg, 0.234 mmole), indole-2-carbonyl chloride (43.1 mg, 0.240 mmole) and triethylamine (33.3 µl, 0.240 mmole) were combined in $CH_2Cl_2$ (3 ml). The reaction was stirred for 10 minutes at room temperature then chromatographed on silica gel (14% acetone in $CH_2Cl_2$). The product fractions were combined and evaporated to dryness in vacuo. The residue was triturated with $Et_2O$ to yield the title compound: (m.p. 160°–171° C.).

TLC: silica gel (15% acetone in $CH_2Cl_2$) $R_f$=0.27
NMR: Consistent with structure
HPLC: 97.6% M.S.: Molecular ion at m/e=438
Anal. Calc'd for $C_{26}H_{22}N_4O_3$.0.1$C_4H_{10}O$.0.25$H_2O$ C, 70.40; H, 5.26; N, 12.44 Found: C, 70.40; H, 5.16; N, 12.15

EXAMPLE 13

(RS)-N-(2,3-Dihydro-1-methyl-2-oxo-5-phenyl-1H-1,4-benzodiazepin-3-yl)-N'-9H-Dyrido(3,4-b)indol-3-yl-urea A solution of (RS)-1,3-dihydro-1-methyl-3-(p-nitrophenyloxycarbonyl)amino-5-phenyl-2H-1,4-benzodiazepin-2-one (100 mg, 0.232 mmole) and 3-amino-β-carboline[1] (45.8 mg, 0.250 mmole) in DMF (5 ml) was treated with triethylamine (48.4 µl, 0.348 mmole) and warmed to 45° C. for 16 hours. After removal of DMF in vacuo, the residue was dissolved in $CH_2Cl_2$ and chromatographed on silica gel (25% acetone in $CH_2Cl_2$). The product fractions were combined and stripped and the title compound crystallized from EtOAc: (m.p. 281°–283° C.).

[1]Dodd, R. H., et al. J. Med. Chem. 28 824 (1985).

TLC: silica gel (160/10/1 of -$CH_2Cl_2$/MeOH/conc. $NH_4OH$) $R_f$=0.24
NMR: Consistent with structure
HPLC: 99.3% pure
M.S.: M+H=475 (FAB)
Anal. Calc'd for $C_{28}H_{22}N_6O_2$.0.20$C_4H_8O_2$ C, 70.28; H, 4.83; N, 17.08 Found: C, 70.10; H, 4.55; N, 17.24

EXAMPLE 14

(RS)-N-(6-Amino-3-pyridyl)-N'-(2,3-dihydro-1-methyl-2-oxo-5-phenyl-1H-1,4-benzodiazepin-3-yl)

2,5-Diaminopyridine dihydrochloride (45.5 mg, 0.250 mmole), (RS)-1,3-dihydro-1-methyl-3-(p-nitrophenyloxycarbonyl)amino-5-phenyl-2H-1,4-benzodiazepin-2-one (100 mg, 0.232 mmole) and triethylamine (110 µl, 0.79 mmole) were combined in DMF (8 ml) and stirred at room temperature for 16 hours. After removal of DMF in vacuo, the residue was treated with 1N NaOH (aqueous) and extracted with EtOAc (3×). The organic layers were combined, washed with brine (1×), dried over $Na_2SO_4$, filtered and evaporated to dryness in vacuo. The crude residue was chromatographed on silica gel eluted with 7% MeOH in $CH_2Cl_2$. The product fractions were combined and evaporated to dryness in vacuo. The residue was crystallized from EtOAc diluted with $Et_2O$ to give the title compound: (m.p. 165°–175° C.).

TLC: silica GF (90/10/1/1 of $CH_2Cl_2$/MeOH/$H_2O$/HOAc) $R_f$=0.22
NMR: consistent with structure
HPLC: 96.3%
M.S.: M+H=401 (FAB)
Anal. Calc'd for $C_{22}H_{20}N_6O_2$.0.35$H_2O$ C, 64.96; H, 5.13; N, 20.66 Found: C, 65.05; H, 5.20; N, 20.66.

EXAMPLE 15

1,3-Dihydro-3-(5-hydroxyindole-2-carbonylamino)-1-methyl-5-phenyl-2H-1,4-benzodiazepin-2-one 3(S)-(−)-3-Amino-1,3-dihydro-1-methyl-5-phenyl-2H-1,4-benzodiazepin-2-one (0.14 g, 0.53 mmol) and 5-hydroxyindole-2-carboxylic acid (0.11 g, 0.63 mmol) were combined in a mixture of $CH_2Cl_2$ (5 ml) and DMF (1 ml). EDC (0.1 g, 0.56 mmol) was added followed by $Et_3N$ sufficient to render the mixture basic (pH 8) to moistened pH detector sticks (E. Merck). The mixture was stirred at ambient temperature for 6 hours, then evaporated to dryness in vacuo. The residue was diluted with aqueous citric acid and extracted with EtOAc. The EtOAc layer was washed twice with saturated sodium bicarbonate which had been diluted 1:1 with water, then dried over sodium sulfate, filtered, and evaporated to dryness in vacuo. The residue was dried in vacuo at 90° C. overnight to give the title compound: (mp 120°–130° C. (↑)).

TLC: Silica gel (10% $CH_3OH$ in $CH_2Cl_2$) $R_f$=0.73
NMR: Consistent with structure, $H_2O$ observed.
HPLC: Greater than 94.5% pure
M.S. Molecular ion at m/e=424
Anal. Calc'd for $C_{25}H_{20}N_4O_3$0.55$H_2O$: C, 69.12; H, 4.90; N, 12.90; Found: C, 69.34; H, 5.01; N, 12.52.

EXAMPLE 15

1,3-Dihydro-3-(5-carboxymethyloxyindole-2-carbonylamino)-1-methyl-5-phenyl-2H-1,4-benzodiazepin-2-one 1,3-Dihydro-3-(5-hydroxyindole-2-carbonylamino)-1-methyl-5-phenyl-2H-1,4-benzodiazepin-2-one (0.1 g, 0.236 mmol) and iodoacetic acid (0.044 g, 0.236 mmol) were combined in dry DMF (2 ml) and treated with sodium hydride (18.8 mg of a 60% suspension in mineral oil; 0.472 mmol). The mixture was stirred at ambient temperature for 1 hour, then evaporated to dryness in vacuo. To the residue were added water, dilute sodium bisulfite solution, then saturated sodium bicarbonate. The aqueous phase was washed with EtOAc, made acidic with 6N HCl, and extracted with EtOAc. The acid layer extract was dried over sodium sulfate, filtered, and evaporated to dryness in vacuo. The residue was chromatographed on silica gel eluted with 180:10:1:1 of $CH_2Cl_2:MeOH:HOAc:H_2O$. The product fractions were evaporated to dryness in vacuo and the residue triturated with ether to give the title compound which was dried in vacuo at 90° C. overnight: (mp 150°-180° C. (↑)).

TLC: Silica gel (180:10:1:1 of $CH_2Cl_2:CH_3OH:$-$HOAc:H_2O$) $R_f=0.19$

NMR: Consistent with structure, $Et_2O$ and $H_2O$ observed.

HPLC: Greater than 83.2% pure

M.S. M+H at m/e=483 (FAB)

Anal. Calc'd for $C_{27}H_{22}N_4O_5.0.05Et_2O.0.7H_2O$: C, 65.49; H, 4.83; N, 11.23; Found: C, 65.53; H, 4.49; N, 11.10.

EXAMPLE 17

N-(2,3-Dihydro-1-(2-hydroxyethyl)-2-oxo-5-phenyl-1H-1,4-benzodiazepin-3-yl)-N'-(3-methylphenyl)-urea 3-(RS)-Amino-1,3-dihydro-1-(2-hydroxyethyl)-5-phenyl-2H-1,4-benzodiazepin-2-one (0.45 g, 1.5 mmol) was dissolved in THF (10 ml) and treated with 3-methylphenylisocyanate (0.207 g, 1.55 mmol), and the mixture stirred at ambient temperature for 1 hour, then evaporated to dryness in vacuo. The residue was chromatographed on silica gel eluted with 20% acetone in $CH_2Cl_2$. The product fractions were evaporated to dryness in vacuo and the residue triturated with ether to give the title compound which was dried in vacuo at 65° C. for 2 hours: (mp 138°-154° C.).

TLC: Silica gel (90:4:0.4:0.4 of $CH_2Cl_2:CH_3OH:$-$HOAc:H_2O$) $R_f=0.24$

NMR: Consistent with structure.

HPLC: Greater than 99.7% pure

M.S. M+H at m/e=429 (FAB)

Anal. Calc'd for $C_{25}H_{24}N_4O_3.0.07 Et_2O.0.4 H_2O$: C, 68.87; H, 5.83; N, 12.71; Found: C, 68.83; H, 5.63; N, 12.58.

EXAMPLE 18

N-(2,3-Dihydro-1-(2-dimethylaminoethyl)-2-oxo-5-phenyl-1H-1,4-benzodiazepin-3-yl)-N'-(3-methoxyphenyl)-urea Sodium hydride (26.4 mg of a 50% dispersion in mineral oil; 0.55 mmol) was stirred under nitrogen in dry DMF (5 ml) in an ice bath. (RS)-1,3-Dihydro-3-(benzyloxycarbonyl)amino-5-phenyl-2H-1,4-benzodiazepin-2-one (0.21 g, 0.54 mmol) in DMF (4 ml) was added, and the mixture stirred 1 hr in the cold. (2-Chloroethyl)-dimethylamine (59.2 mg, 0.55 mmol), prepared by distillation of a mixture of the hydrochloride and powdered sodium hydroxide in vacuo, was added and the mixture stirred 1 hr in the cold, and overnight at ambient temperature. The DMF was removed in vacuo and the residue was treated with water and extracted with ethyl acetate. The ethyl acetate layer was washed with water, dried over sodium sulfate, filtered, and evaporated to dryness in vacuo. The residue was chromatographed on silica gel eluted with 90:10:1:1 of $CH_2Cl_2:MeOH:H_2O:HOAc$ and the product fractons were evaporated to dryness in vacuo to provide (RS)-1-(2-chloroethyl)-1,3-dihydro-3-(benzyloxycarbonyl) amino-5-phenyl-2H-1,4-benzodiazepin-2-one. This compound (120 mg, 0.268 mmol) was added to a suspension of 10% palladium/Carbon (70 mg) in 4.5% methanolic formic acid (5 ml) stirred at ambient temperature under nitrogen. After 25 min, the mixture was filtered and the filtrate evaporated to dryness in vacuo. The residue was treated with saturated sodium carbonate solution and extracted with ethyl acetate. The combine ethyl acetate layers were washed with water, dried over sodium sulfate, filtered, and evaporated to dryness in vacuo. The residue was dissolved in THF, cooled in an ice bath, and treated with 3-methoxyphenylisocyanate (35.1 μl). The mixture was stirred in the cold for 30 min. warmed to ambient temperature, and filtered. The filtrate was evaporated to dryness in vacuo, and the residue was treated with ether (30 ml) and re-evaporated three times. The residue was triturated with ether and filtered, and the resulting solid dried at 65° C. overnight to provide the title compound: (mp 213°-215° C.). TLC: Silica gel (80:10:1 of $CH_2Cl_2:CH_3OH:NH_3$) $R_f=0.41$ NMR: Consistent with structure.

HPLC: Greater than 99.3% pure

M.S. M+H at m/e=472 (FAB)

Anal. calc'd for $C_{27}H_{29}N_5O_3$: C, 68.77; E, 6.20; N, 14.85; Found: C, 68.43; H, 6.30; N, 14.75.

EXAMPLE 19

(R)-3-((((2,3-Dihydro-1-methyl-2-oxo-5-phenyl-1H-1,4-benzodiazepin-3-yl)amino)carbonyl)amino)benzoic acid ethyl ester (R)-1,3-Dihydro-1-methyl-3-(p-nitrophenyloxycarbonyl)amino-5-phenyl-2H-1,4-benzodiazepin-2-one (150 mg, 0.35 mmol), 3-aminobenzoic acid ethyl ester (61 mg, 0.37 mmol), and triethylamine (52.5 mg, 0.52 mmol) were combined in DMF (2 ml) and heated at 45° overnight. The DMF was removed in vacuo and the residue crystallized from ethyl acetate to provide the title compound: (mp 140°-142° C.).

TLC: Silica gel (1:1 ethyl acetate:hexane) $R_f=0.27$

NMR: Consistent with structure.

HPLC: Greater than 96.6% pure

M.S. Molecular ion at m/e=456

Anal. calc'd for $C_{26}H_{24}N_4O_4 0.5H_2O$: C, 67.09; H, 5.41; N, 12.04; Found: C, 67.09; H, 5.25; N, 11.87.

EXAMPLE 20

(R)-3-((((2,3-Dihydro-1-methyl-2-oxo-5-phenyl-1H-1,4-benzodiazepin-3-yl)amino)carbonyl)amino)phenylacetic acid (R)-1,3-Dihydro-1-methyl-3-(p-nitrophenyloxycarbonyl)amino-5-phenyl-2H-1,4-benzodiazepin-2-one (1.92 g, 4.47 mmol) was dissolved in THF (25 ml) and treated with a solution of (3-aminophenyl)acetic acid methyl ester (670 mg, 4.06 mmol) in THF (5 ml) followed by triethylamine (615 mg, 6.09 mmol). The mixture was stirred at ambient temperature for 4 days. The solvent was removed in vacuo and the residue was treated with water (20 ml) and extracted with ethyl acetate. The combined ethyl acetate layers were washed with 1M NaOH, then with 10% citric acid, dried over sodium sulfate, filtered and evaporated to dryness in vacuo. The residue was chromatographed on silica gel eluted with 1:1 hexane:ethyl acetate. The product fractions were combined and evaporated to dryness in vacuo and the residue crystallized from ethyl acetate to give (R)-3-((((2,3-Dihydro-1-methyl-2-oxo-5-phenyl-1H-1,4-benzodiazepin-3-yl)amino)carbonyl-)amino)phenyl acetic acid methyl ester. This ester (885mg, 1.94mmol) was dissolved in THF (5 ml) and treated with a solution of lithium hydroxide (815 mg, 19.4 mmol) in water (10 ml). The mixture was stirred at ambient temperature for 3 hours, diluted with water (100 ml), acidified with 1N HCl, and extracted with ethyl acetate. The ethyl acetate layers were washed with brine, dried over sodium sulfate, filterate, and evaporated to dryness in vacuo. The residue was chromatographed on silica gel eluted with chloroform followed by 9:1 chloroform:methanol. The product fractions were combined and evaporated to dryness in vacuo. The residue was crystallized from ethyl acetate to provide the title compound: (mp 167°–170° C.).

TLC: Silica gel (1:1 ethyl acetate:hexane) single component.

NMR: Consistent with structure.

HPLC: Greater than 97% pure.

M.S. M+H at m/e=443(FAB).

Anal. Calc'd for $C_{25}H_{22}N_4O_4 \cdot 0.55EtOAc$: C, 66.54; H, 5.42; N, 11.41; Found: C, 66.15; H, 5.04; N, 11.63.

While the foregoing specification teaches the principles of the present invention, with examples provided for the purpose of illustration, it will be understood that the practice of the invention encompasses all of the usual variations, adaptations or modifications, as come within the scope of the following claims and its equivalents.

EXAMPLE 21

(R)-N-(2,3-Dihydro-1H-inden-5-yl)N'-(2,3-dihydro-1-methyl-2-oxo-5-phenyl-1H-1,4-benzodiazepin-3-yl)-urea (R)-1,3-Dihydro-1-methyl-3-(p-nitrophenyloxycarbonyl)amino-5-phenyl-2H-1,4-benzodiazepin-2-one (200 mg. 0.46 mmole) was dissolved in 2 ml of freshly degassed, dry N,N-dimethylformamide (DMF) and treated with 1 ml of DMF containing 74 mg (0.50 mmole) of 5-aminoindane and 97.4 µl of triethylamine. The resulting solution was stirred under nitrogen for four hours. The reaction mixture was poured into 75 ml of water and extracted with ethyl acetate (3×40 ml). The combined organic extracts were washed with 1N sodium hydroxide solution (4×100 ml), 10% citric acid solution (2×100 ml), and brine. The organic extracts were then dried and the residue was plug-filtered through a six inch silica gel column. The eluate was concentrated and the residue was crystallized from a methylene chloride-ether mixture to give the title compound: mp 156°–158° C. NMR: Structure is consistent with the spectrum.

FAB MS: 425 (M++H).

Anal. Calc'd for $C_{26}H_{24}N_4O_2$: Calc'd: C, 73.56; H, 5.69; N, 13.20, Found: C, 73.26; H, 5.81; N, 13.04.

What is claimed is:

1. A compound of Formula:

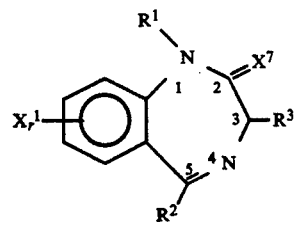

wherein:

$R^1$ is H, $C_1$–$C_6$ linear or branched alkyl, loweralkenyl, lower alkynyl, $X^{12}$-COOH, —$X^{12}$COOR$^6$, —$X^{11}$-cycloloweralkyl, —$X^{12}$NR$^4$R$^5$, —$X^{12}$CONR$^4$R$^5$, —$X^{12}$CN, or —$X^{11}$CX$_3{}^{10}$;

$R^2$ is H, loweralkyl, substituted or unsubstituted phenyl (wherein the substituents may be 1 or 2 of halo, loweralkyl, loweralkoxy, loweralkythio, carboxyl, carboxyloweralky, nitro, —CF$_3$, or hydroxy), 2-,3-, or 4-pyridyl;

$R^3$ is

—NH(CH$_2$)$_2$—$_3$NHCOR$^7$,

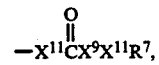

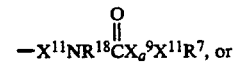

—$X^{11}$NR$^{18}$SO$_2$(CH$_2$)$_q$R$^7$;

$R^4$ and $R^5$ are independently H or $R^6$ or in combination with the N of the NR$^4$R$^5$ group form an unsubstituted or mono or disubstituted, saturated or unsaturated, 4–7 membered heterocyclic ring, wherein said heterocyclic ring may contain a second heteroatom selected from O and NCH$_3$ and the substituents(s) is/are independently selected from $C_1$–$C_4$alkyl;

$R^6$ is loweralkyl, cycloloweralkyl, substituted or unsubstituted phenyl, or substituted or unsubstituted phenylloweralkyl wherein the phenyl or phenyl-loweralkyl substituents may be 1 or 2 of halo, loweralkyl, loweralkoxy, nitro, or CF$_3$;

$R^7$ is

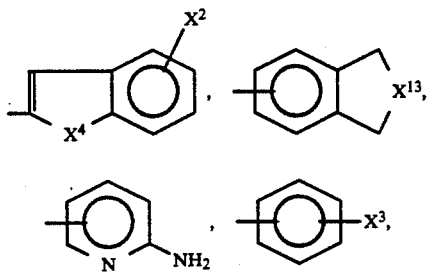

or

-continued

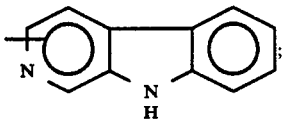

$R^8$ is H, loweralkyl, cycloloweralkyl, —$X^{13}CONH_2$, —$X^{13}COOR^6$, —$X^{13}COOH$, —$X^{13}$-cycloloweralkyl, or —$X^{13}NR^4R^5$,
$R^{15}$ is H, or loweralkyl,
$R^{18}$ is H or loweralkyl;
n is 1–6,
q is 0–4;
r is 1 or 2;
$X^1$ is H,—$NO_2$,$CF_3$, CN, OH, loweralkyl, halo, loweralkylthio, loweralkoxy, —$X^{11}COOR^6$, $X^{11}COOH$, or —$X^{11}NR^4R^5$,
$X^2$ is H or $X^3$, with the proviso that when $X^2$ is H, then $X^4$ is $NX^5COOH$ or $NX^5COOR^6$ wherein $X^5$ is a linear alkyl chain of 2 to 6 carbon atoms, any carbon atom of which may be additionally substituted with a linear or branched alkyl group of 1 to 3 carbon atoms;
$X^3$ is $O(CH_2)_nCOOR^6$, $O(CH_2)_nCOOH$, $(CH_2)_nCOOR^6$, $(CH_2)_nCOOH$, $COOR^6$, or $X^{12}OR^6$;
$X^4$ is S,O, $CH_2$, or $NR^8$;
$X^7$ is O,S, HH, or $NR^{15}$ with the proviso that $X^7$ can be $NR^{15}$ only when $R^1$ is not H;
$X^8$ is H, loweralkyl;
$X^9$ and $X_a^9$ are independently $NR^{18}$ or O;
$X^{10}$ is F, Cl, or Br;
$X^{11}$ is absent or $C_{1-4}$ linear or branched alkyl alkylidene;
$X^{12}$ is $C_{1-4}$ linear or branched alkylidene,
$X^{13}$ is linear or branched alkylidene.

2. A compound according to claim 1, wherein:
$R^1$ is H, $C_1$-$C_6$ linear or branched alkyl, —$X^{12}COOR^6$, —$X^{11}$-cycloloweralkyl, $X^{12}NR^4R^5$, —$X^{12}CONR^4R^5$, or $X^{12}COOH$;
$R^2$ is substituted or unsubstituted phenyl (wherein the substituents may be 1 or 2 of halo, loweralkyl, loweralkoxy, loweralkylthio, carboxyl, carboxyloweralkyl, nitro, —$CF_3$ or hydroxy), 2-,3-, or 4-pyridyl;
$R^3$ is

—NH(CH$_2$)$_{2-3}$NCOR$^7$, or

$R^4$ and $R^5$ are independently H or $R^6$ or in combination with the N or the $NR^4R^5$ group form an unsubstituted or mono or disubstituted, saturated or unsaturated, 4–7 membered heterocyclic ring, wherein said heterocyclic ring may contain a second heteroatom selected from O and $NCH_3$ and the substituents(s) is/are independently selected from $C_1$-$C_4$ alkyl;
$R^6$ is $C_{1-4}$ straight or branched-chain alkyl or $C_3$-$C_6$ cycloalkyl

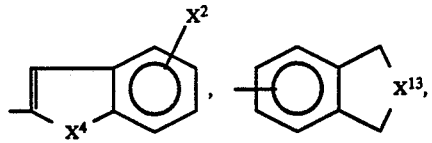

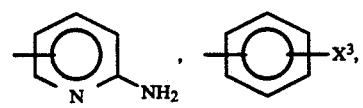

or

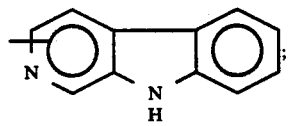

$R^8$ is H, loweralkyl, cycloloweralkyl, $X^{13}COOR^6$, $X^{13}COOH$, or $X^{13}NR^4R^5$;
$R^{18}$ is H or loweralkyl;
n is 1–3;
q is 0–3;
r is 1 or 2;
$X^1$ is H, —$NO_2$, $CF_3$, CN, loweralkyl, halo, loweralkylthio —$X^{11}COOR^6$, $X^{11}COOH$, or $X^{11}NR^4R^5$;
$X^2$ is H or $X^3$ with the proviso that when $X^2$ is H, then $X^4$ is $NX^5COOH$ or $NX^5COOR^6$ wherein $X^5$ is a linear alkyl chain of 2 to 4 carbon atoms, any carbon atom of which may be additionally substituted with a linear or branched alkyl group of 1 to 3 carbon atoms;
$X^3$ is $O(CH_2)_nCOOR^6$, $O(CH_2)_nCOOH$, $(CH_2)_nCOOR^6$, $(CH_2)_nCOOH$, or $COOR^6$;
$X^4$ is S, O, or $NR^8$;
$X^7$ is O;
$X^9$ and $X_a^9$ are independently $NR^{18}$, or O;
$X^{11}$ is absent or $C_{1-4}$ linear or branched alkylidene;
$X^{12}$ is $C_{1-4}$ linear or branched alkylidene;
$X^{13}$ is linear or branched alkylidene or pharmaceutically acceptable salt thereof.

3. A method of antagonizing the binding of cholecystokinins to cholecystokinin receptors or antagonizing the binding of gastrin to gastrin receptors which comprises contacting said cholecystokinin receptors or said gastrin receptors, respectively, with a compound of claims 1 or 2.

4. A pharmaceutical composition useful in the treatment of disorders of gastric secretion, appetite regulation, gastrointestinal motility, pancreatic secretion, and dopaminergic function, comprising a pharmaceutical carrier, and dispersed therein, a therapeutically effective amount of a compound of claims 1 or 2.

* * * * *